United States Patent [19]

Schulthess et al.

[11] Patent Number: 5,059,698

[45] Date of Patent: Oct. 22, 1991

[54] UNSATURATED BETA-KETO-ESTER ACETALS

[75] Inventors: Adrian Schulthess, Tentlingen; Max Hunziker, Düdingen, both of Switzerland

[73] Assignee: Ciba-Geigy Corporation, Ardsley, N.Y.

[21] Appl. No.: 363,801

[22] Filed: Jun. 9, 1989

[30] Foreign Application Priority Data

Jun. 13, 1988 [CH] Switzerland .......................... 2257/88

[51] Int. Cl.$^5$ .................. C07D 317/22; C07D 319/04; C07F 69/708
[52] U.S. Cl. .................................... 549/375; 549/447; 560/187
[58] Field of Search ................. 549/375, 447; 560/187

[56] References Cited

U.S. PATENT DOCUMENTS

| | | | |
|---|---|---|---|
| 3,779,778 | 12/1973 | Smith et al. | 96/115 R |
| 4,247,611 | 1/1981 | Sander et al. | 430/286 |
| 4,248,957 | 2/1981 | Sander et al. | 430/270 |
| 4,294,909 | 10/1981 | Lee | 430/291 |
| 4,311,782 | 1/1982 | Buhr et al. | 430/270 |
| 4,356,252 | 10/1982 | Lee | 430/290 |
| 4,737,426 | 4/1988 | Roth | 430/17 |

FOREIGN PATENT DOCUMENTS 2342068  4/1974  Fed. Rep. of Germany .

OTHER PUBLICATIONS

Kosar, "Light Sensitive Systems," John Wiley & Sons, N.Y. pp. 339–352 (1965).
Chem. Abst. 87:68333n (1977).
C. A. 98:126774x (1983).
F. Gasparrini et al., Tetrahedron, vol. 40, pp. 1491–1500 (1984).
J. Org. Chem., vol. 49, pp. 5102–5105 (1984).
C. A. 78: 148429c (1973).
C. A. 82: 77588y (1975).

Primary Examiner—David B. Springer
Attorney, Agent, or Firm—JoAnn Villamizar

[57] ABSTRACT

Polymeric β-keto-ester acetals which, in combination with compounds which release acid under the action of actinic radiation, are suitable as positive photoresists, which are suitable for the production of printing plates, printed circuit boards, integrated circuits or silver-free films, can be prepared by free-radical polymerization from compounds of the formula I or II

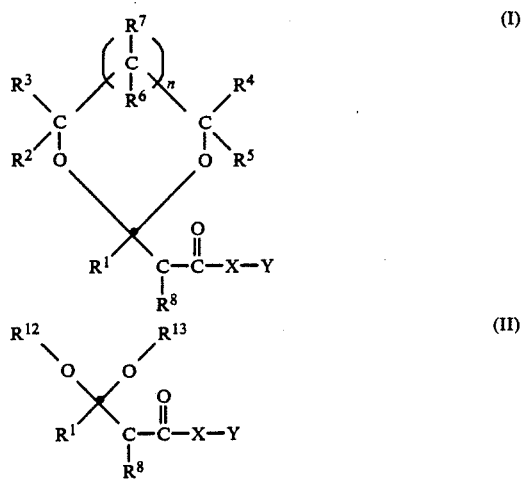

in which n is zero, 1 or 2 and, for example, $R^1$ is an H atom, $C_1$–$C_{10}$-alkyl, phenyl or benzyl, $R^2$, $R^3$, $R^4$, $R^5$, $R^6$, $R^7$ and $R^8$ independently of one another are each an H atom, halogen atom, $C_1$–$C_{10}$alkyl, phenyl, naphthyl or the radical —COOR$^9$,

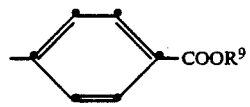

or —SO$_2$R$^9$, in which R$^9$ is $C_1$–$C_6$alkyl or phenyl, X is O, S or NR$^{10}$, in which R$^{10}$ is an H atom, $C_1$–$C_6$alkyl or phenyl, Y is a radical of the following formulae

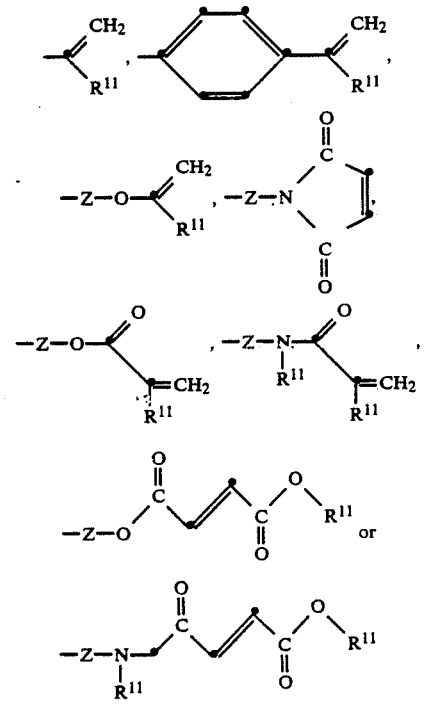

in which R$^{11}$ is an H atom, $C_1$–$C_6$alkyl or phenyl and Z is an aliphatic radical containing at least two methylene groups, and R$^{12}$ and R$^{13}$ independently of one another are each $C_1$–$C_{10}$alkyl, phenyl or naphthyl.

3 Claims, No Drawings

UNSATURATED BETA-KETO-ESTER ACETALS

The present invention relates to unsaturated β-keto-ester acetals, to the polymeric β-keto-ester acetals obtained therefrom by homopolymerization or copolymerization, to positive photoresists containing the polymeric β-keto-ester acetals as solution inhibitors and to the use of the phororesists for the production of printed circuit boards, integrated circuits, printing formers or as silver-free photographic films.

In photoresists capable of aqueous development, a film-forming, water-soluble or water/alkali-soluble resin is, as is known, mixed with a solution inhibitor which greatly reduces the solubility of the mixture in an aqueous-alkaline developer. As a result of a photochemical reaction, the solution inhibitor is changed in such a way that, for example by depolymerization, acetal cleavage, ortho-ester cleavage or formation of a carboxylic acid from an o-quinone-diazide, the photoresist is readily soluble again in the developer in the exposed areas.

Examples of known solution inhibitors for positive photoresists are naphthoquinone-diazides (cf. J. Kosar in "Light-Sensitive Systems", published by John Wiley & Sons, New York, 1965, pages 339 to 352) in novolak resins. Napthoquinones are photoactive and act as a solution inhibitor in the unexposed areas in the photoresist. However, they are temperature-sensitive and have only a low storage stability. Since, in addition, they absorb light very strongly, they cannot be applied in thick layers.

For positive photoresists, U.S. Pat. No. 3,779,778 describes solution inhibitors which are obtained by adding a bisphenol or polyphenol, a compound containing monoalkylsulfonamide groups or certain secondary amines to compounds containing vinyl ether groups, especially to tetrahydropyranyl ethers. Apart from the fact that the synthesis of these solution inhibitors is involved, these are relatively insensitive in thick layers and require long exposure times.

German Offenlegungsschrift 2,718,254 discloses polyaddition products or polycondensation products with recurrent acetal units or ketal units in the main chain as solution inhibitors for positive photoresists. Again, unless the photoresist is applied in thin layers, these solution inhibitors are no longer highly sensitive, so that relatively long exposure times must be accepted.

The solution inhibitors known from German Offenlegungsschrift 2,829,511 are low-molecular enol ether compounds. Monomeric solution inhibitors involve the risk of them diffusing out of the carrier polymer, so that photographic films containing such solution inhibitors are not very stable.

The cyclic acetals and ketals of β-keto-esters, disclosed in EP-A 0,202,196, are also monomeric compounds and are thus affected by the same disadvantage as the abovementioned solution inhibitors for photoresists.

It has been found that certain unsaturated β-keto-ester acetals can, alone or together with other olefinically unsaturated compounds, be polymerized to give polymeric β-keto-ester acetals, which represent valuable solution inhibitors for positive-working photoresist systems.

The present invention thus relates to novel compounds of the formula I or II

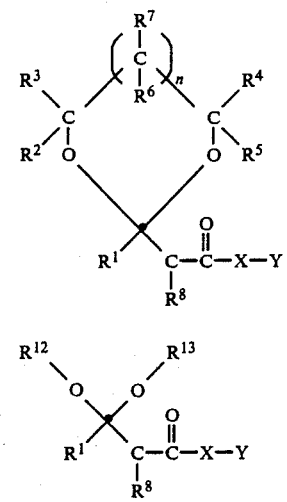

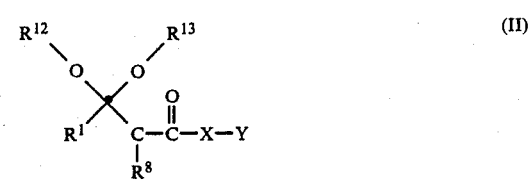

in which n is zero or the number 1 or 2, $R^1$ is a hydrogen atom, a $C_1$–$C_{10}$alkyl which is unsubstituted or substituted by halogen atoms, a $C_2$–$C_{10}$alkyl which is interrupted by ether oxygen atoms, or a phenyl or benzyl which is unsubstituted or substituted by halogen atoms, nitro groups, $C_1$–$C_4$alkyl or $C_1$–$C_4$alkoxy, $R^2$, $R^3$, $R^4$, $R^5$, $R^6$, $R^7$ and $R^8$ independently of one another are each a hydrogen atom, a halogen atom, a $C_1$–$C_{10}$alkyl which is unsubstituted or substituted by halogen atoms, a phenyl or naphthyl which is unsubstituted or substituted by halogen atoms, cyano groups, nitro groups or $C_1$–$C_4$alkyl, or a radical of the formulae —$COOR^9$,

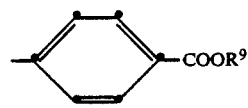

or —$SO_2R^9$, in which $R^9$ is a $C_1$–$C_6$alkyl or phenyl which is unsubstituted or substituted by halogen atoms or nitro groups, X is O, S or $NR^{10}$, $R^{10}$ being a hydrogen atom or a $C_1$–$C_6$alkyl or phenyl which is unsubstituted or substituted by halogen atoms or nitro groups, and Y is a radical of the following formulae

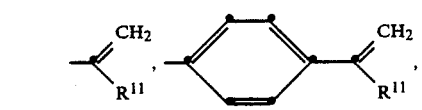

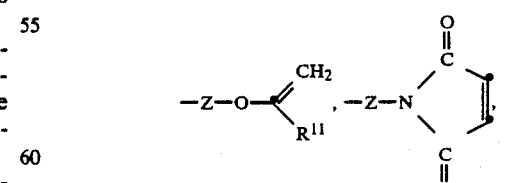

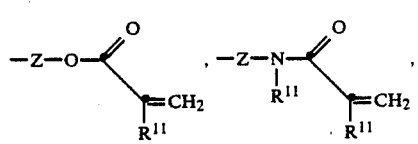

-continued

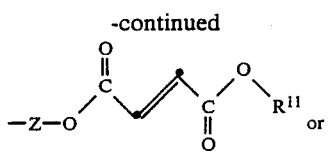 or

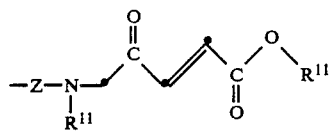

in which $R^{11}$ is a hydrogen atom or a $C_1$–$C_6$alkyl or phenyl which is unsubstituted or substituted by halogen atoms or nitro groups, Z is an aliphatic radical which is unsubstituted or substituted by halogen atoms, nitro groups or phenyl and contains at least two methylene groups, or an aliphatic radical which is unsubstituted or substituted by halogen atoms or nitro groups, contains at least two methylene groups and is interrupted by ether oxygen atoms, phenylene or cyclohexylene groups, and $R^{12}$ and $R^{13}$ independently of one another are each a $C_1$–$C_{10}$alkyl, phenyl or naphthyl which is unsubstituted or substituted by halogen atoms or nitro groups.

Preferred compounds of the formula I or II are those in which n is zero or the number 1, $R^1$ is a hydrogen atom, a $C_1$–$C_4$alkyl which is unsubstituted or substituted by a chlorine atom or atoms, a $C_2$–$C_4$alkyl interrupted by an ether oxygen atom or atoms, phenyl or benzyl, $R^2$, $R^3$, $R^4$, $R^5$, $R^6$ and $R^7$ independently of one another are each a hydrogen atom, chlorine atom, $C_1$–$C_6$alkyl or phenyl, $R^8$ is a hydrogen atom, phenyl, p-nitrophenyl, p-cyanophenyl or the radical —COOR$^9$, in which $R^9$ is $C_1$–$C_6$alkyl or phenyl, X is an oxygen atom, Y is a radical of the formulae formulae

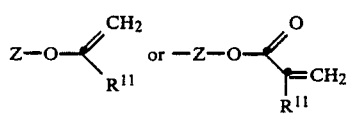

in which $R^{11}$ is a hydrogen atom or $C_1$–$C_4$alkyl, Z is one of the following radicals —(CH$_2$)$_b$—, —CH$_2$—(CH$_2$—OCH$_2$—)$_c$CH$_2$—, OCH$_2$—CH$_2$—, —CH$_2$—CHR$^{11}$—,

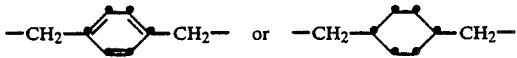

in which b is a number from 3 to 5 and c is zero or a number from 1 to 3, and $R^{12}$ and $R^{13}$ independently of one another are each $C_1$–$C_4$alkyl.

Compounds of the formula I, wherein n is zero or the number 1, $R^1$ is $C_1$–$C_4$alkyl, methoxymethyl or phenyl, $R^2$, $R^3$, $R^4$, $R^5$, $R^6$, $R^7$ and $R^8$ are a each hydrogen, X is an oxygen atom and Y is the radical

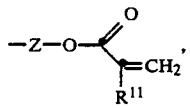

in which Z is ethylene and $R^{11}$ is a hydrogen atom or methyl, represent particularly preferred compounds.

Likewise, those compounds of the formula II are particularly preferred in which $R^1$, $R^{12}$ and $R^{13}$ independently of one another are each $C_1$–$C_4$alkyl, $R^8$ is a hydrogen atom, X is an oxygen atom and Y is a radical of the formula

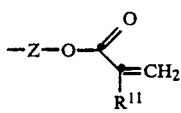

in which Z is ethylene and $R^{11}$ is a hydrogen atom or methyl.

Unsubstituted or substituted alkyl $R^1$ to $R^{11}$ are straight-chain or branched-chain radicals, for example methyl, ethyl, 2-chloro- or 2-bromo-ethyl, n-propyl, isopropyl, n-butyl, sec-butyl, tert-butyl, n-pentyl, iso-amyl, n-hexyl, n-octyl or 2-nitroethyl.

Examples of substituted phenyl or substituted benzyl radicals $R^1$ to $R^{11}$ are 2-, 3- or 4-chlorophenyl, 2-, 3- or 4-chlorobenzyl, 2-, 3- or 4-nitrophenyl, 2-, 3- or 4-cyanophenyl, 2-, 3- or 4-nitrobenzyl and 2- or 4-methoxybenzyl.

Examples of substituted naphthyl $R^2$ to $R^8$ are α-chloronaphthyl or α-nitronaphthyl.

An aliphatic radical Z is, for example, alkylene such as ethylene, isopropylene or butylene, or an oxyalkylene or poly(oxy)alkylene containing 2 to 10 $C_2$ to $C_5$oxyalkylene units.

The unsaturated β-keto-ester acetals according to the invention are prepared by known processes. The compounds of the formulae I and II, according to the invention can be, for example, and are preferably prepared by a) reacting a compound of the formula III

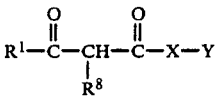  (III)

in which $R^1$, $R^8$, X and Y are as defined in formula I, either with a compound of the formula IV

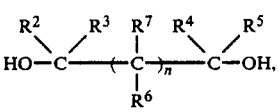  (IV)

in which n, $R^2$, $R^3$, $R^4$, $R^5$, $R^6$ and $R^7$ are as defined in formula I, to give a compound of the formula I, at least 1 mol of a compound of the formula IV being employed per 1 mol of the compound of the formula III, or with compounds of the formulae V and VI

HO—R$^{12}$  (V)

and

OH—R$^{13}$  (VI), in which $R^{12}$ and $R^{13}$ are as defined in formula II, to give a compound of the formula II, at least 2 mol of the compounds of the formulae V and VI being employed per 1 mol of the compound III.

b) reacting compounds of the formula VII or VIII

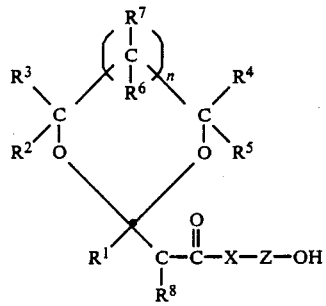

(VII)

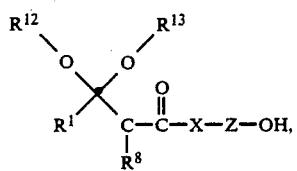

(VIII)

in which n, $R^1$, $R^2$, $R^3$, $R^4$, $R^5$, $R^6$, $R^7$, $R^8$, $R^{12}$, $R^{13}$, X and Z are as defined in the formulae I and II, with a compound of the formula IX, X or XI

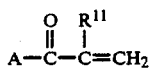

(IX)

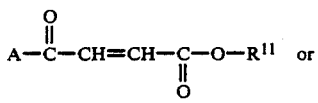 or (X)

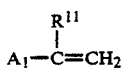

(XI)

in which $R^{11}$ is as defined in formula I or II, A is a halogen atom or a hydroxyl group, it also being possible for the compounds of the formulae IX and X to be in the form of an anhydride, and $A_1$ is a halogen atom or $C_1$-$C_4$alkoxy, in molar quantities to give compounds of the formula I or II, or by c) reacting compounds of the formula XII or XIII

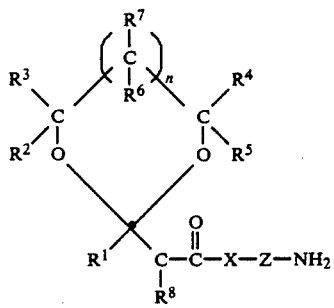

(XII)

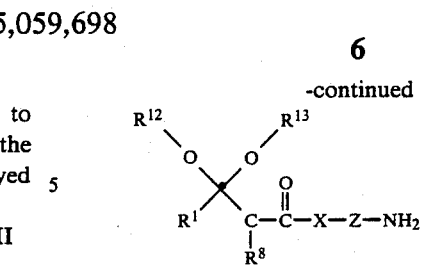

(XIII)

in which n, $R^1$, $R^2$, $R^3$, $R^4$, $R^5$, $R^6$, $R^7$, $R^8$, $R^{12}$, $R^{13}$, X and Z are as defined in formulae I and II, with maleic anhydride, a compound of the formula XI or X or the anhydride thereof in molar quantities to give compounds of the formula I or II.

The acetalization of a compound of the formula III with a compound of the formula IV or compounds of the formulae V and VI is preferably carried out in the presence of an acidic catalyst, for example an acid such as sulfuric acid, hydrochloric acid, acetic acid or p-toluenesulfonic acid. Other catalysts which can be used are salts of p-toluenesulfonic acid, for example pyridinium p-toluenesulfonate (PPTS), salts of hydrochloric acid or hydrochlorides of amines. The conversion reaction can be carried out in the absence or presence of a solvent. For the preparation of the unsaturated β-keto-ester acetals of the formula I, those solvents are preferably used which form azeotropes with water, for example dichloromethane, benzene, toluene, xylene or p-chlorobenzene. For the preparation of the unsaturated β-keto-acetals of the formula II, the solvent used is preferably the alcohol serving for the acetalization.

The acetalization of a compound of the formula III can in principle be carried out by any usual process. For example by reacting a β-keto-ester with ortho-esters, acetals or enol ethers of the particular β-keto-ester being obtained depending on the reaction procedure, transacetalization with other acetals under acid catalysis and distilling off the ketone being formed, and by reacting an enol ether of a β-keto-ester with an alcohol under acid or base catalysis.

The compounds of the formulae III, IV, V and VI are known compounds, some of which are commercially available or can be prepared by known methods. A compound of the formula III can be prepared, for example, by transesterifying ethyl acetoacetate with ethylene glycol and esterifying the resulting β-hydroxyethyl acetoacetate with methacrylic acid or an activated acid derivative of methacrylic acid, or by reacting β-hydroxyethyl methacrylate with a diketene.

The compounds of the formulae VII, VIII, XII and XIII are also known and can be prepared, for example, by reacting molar quantities of acetals of the formula VIIa or VIIIa

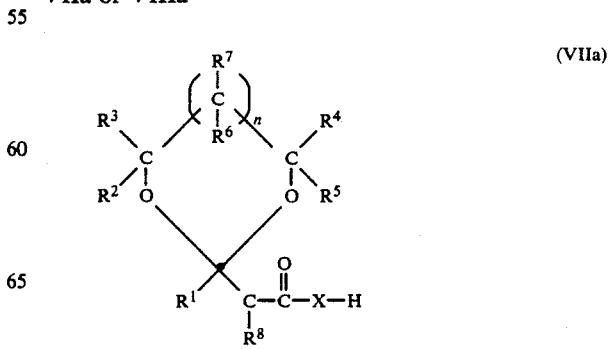

(VIIa)

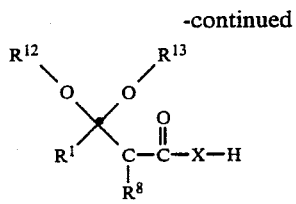 (VIIIa)

in which, n, $R^1$, $R^2$, $R^3$, $R^4$, $R^5$, $R^6$, $R^7$, $R^8$, $R^{12}$, $R^{13}$ and X are as defined in formulae I and II, with a diol of the formula HO—Z—OH, an amino alcohol of the formula HO—Z—NH$_2$ or a diamine of the formula H$_2$N—Z—NH$_2$, in which Z is as defined in formula VII or VIII.

The compounds of the formulae IX to XI represent (meth)acrylic acid and derivatives thereof (IX), maleic acid and derivatives thereof (X) and vinyl compounds, for example a vinyl ether or vinyl chloride.

As mentioned at the outset, polymeric β-keto-ester acetals can be prepared from the acetals of the formulae I and II by polymerization, if appropriate in the presence of olefinically unsaturated comonomers.

The present invention therefore also relates to polymeric β-keto-ester acetals of a molecular weight (Mw) from 1500 to 1,000,000, measured by gel permeation chromatography with polystyrene as standard, which contain, relative to the total quantity of the structural units present in the polymer, 100 to 5 mol % of the recurrent structural unit of the formula XIV or XV

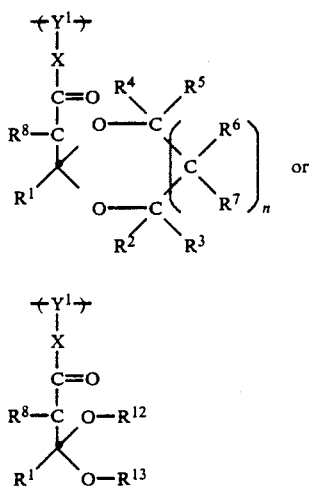

and 95 to 0 mol % of the recurrent structural unit of the formula XVI

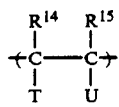 (XVI)

in which n, $R^1$, $R^2$, $R^3$, $R^4$, $R^5$, $R^6$, $R^7$, $R^8$, $R^{12}$, $R^{13}$ and X are as defined in formulae I and II and $Y^1$ is a radical of the following formulae

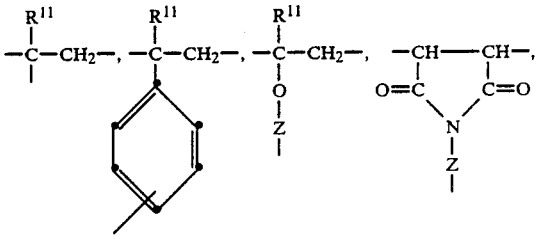

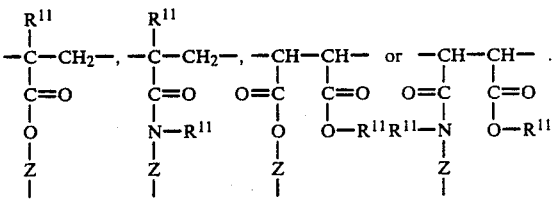

in which $R^{11}$ and Z are as defined above, $R^{14}$ and $R^{15}$ independently of one another are each a hydrogen atom, a C$_1$-C$_4$alkyl which is unsubstituted or substituted by halogen atoms, cyano groups or nitro groups, or a phenyl or naphthyl which is unsubstituted or substituted by halogen atoms, C$_1$-C$_4$alkoxy, hydroxy, cyano or nitro groups, T and U, independently of one another are each a hydrogen atom, a C$_1$-C$_{12}$alkyl which is unsubstituted or substituted by halogen atoms, cyano groups or nitro groups, a phenyl, naphthyl or benzyl which is unsubstituted or substituted by halogen atoms, hydroxy, cyano or nitro groups, C$_1$-C$_4$alkyl or C$_1$-C$_4$alkoxy, or one of the following radicals —OR$^{18}$, —COOR$^{19}$ or —COR$^{20}$, R$^{18}$ and R$^{19}$ independently of one another each being a hydrogen atom, a C$_1$-C$_{12}$alkyl which is unsubstituted or substituted by halogen atoms, cyano groups or nitro groups, or a phenyl or naphthyl which is unsubstituted or substituted by halogen, cyano groups, nitro groups, C$_1$-C$_4$alkyl or C$_1$-C$_4$alkoxy, and R$^{20}$ is as defined for R$^{18}$, and in addition if the radical

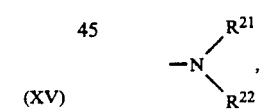

in which $R^{21}$ and $R^{22}$ independently of one another are as defined for $R^{18}$.

The polymeric β-keto-ester acetals according to the invention preferably have a molecular weight (Mw) from 5000 to 500,000, in particular from 20,000 to 150,000.

Moreover, the polymeric β-keto-ester acetals according to the invention preferably contain 100 to 20 mol %, in particular 100 to 50 mol %, of the recurrent structural units of the formula XIV or XV, and 80 to 0 mol %, in particular 50 to 0 mol %, of the recurrent structural units of the formula XVI.

In the recurrent structural units of the formulae XIV and XV, the same preferred definitions as in formulae I and II apply to n, $R^1$, $R^2$, $R^3$, $R^4$, $R^5$, $R^6$, $R^7$, $R^8$, $R^{12}$, $R^{13}$ and X.

The radical $Y^1$ is preferably a radical of the formulae

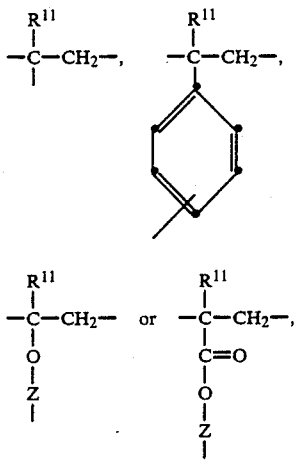

the radical shown last being particularly preferred for $Y^1$.

Alkyl $R^{14}$, $R^{15}$, T and U in the structural unit of the formula XVI is a straight-chain or branched-chain, preferably a straight-chain, alkyl radical.

Halogen atom substituents can be fluorine, chlorine, bromine or iodine, and preferably are chlorine or bromine.

Examples of unsubstituted or substituted alkyl are methyl, ethyl, 2-chloroethyl, 2-nitroethyl, n-propyl, isopropyl, n-butyl, sec-butyl, tert-butyl, n-pentyl, isoamyl, n-hexyl, 2-ethylhexyl, n-decyl, 6-nitrohexyl or 9-bromononyl.

Examples of substituted phenyl or naphthyl are o-, m- or p-chlorophenyl, o-, m- or p-tolyl, xylyl, 2-nitrophenyl or α-chloronaphthyl.

The polymeric β-keto-ester acetals according to the invention can be prepared by free-radical polymerization in a known manner of compounds of the formula I or II or mixtures of compounds of the formula I or II, containing up to 95 mol %, preferably up to 80 mol % and especially up to 50 mol %, of compounds of the formula XVIa

     (XVIa)

in which $R^{14}$, $R^{15}$, T and U are as defined in formula XVI.

The free-radical polymerization can be carried out by application of various techniques. These have been described, for example, by S. Sandler and W. Karo in "Polymer Synthesis", Vol. 1-3, 1968, Academic Press, New York. Examples of conventional polymerization processes are polymerization in bulk or in solvents, emulsion polymerization, suspension polymerization or precipitation polymerization.

The compounds of the formula XVIa are known, and some of them are commercially available. In addition to olefins, for example ethylene or propylene, especially the vinyl compounds may be mentioned as examples of compounds of the formula XVIa. Examples of such monomers are the styrene types, for example styrene, α-methylstyrene, p-methylstyrene or p-hydroxyphenylstyrene, α,β-unsaturated acids and esters of amides thereof, for example acrylic acid, methyl acrylate, acrylamide, the corresponding methacrylic compounds, maleic acid, methyl maleate, maleimides or p-hydroxyphenylmaleimides, halogen-containing vinyl compounds, for example vinyl chloride, vinyl fluoride, vinylidene chloride or vinylidene fluoride, and vinyl esters, for example vinyl acetate or vinyl ethers, for example methyl vinyl ether or butyl vinyl ether.

Examples of further suitable compounds are the allyl compounds such as allyl chloride, allyl bromide or allyl cyanide.

The polymerization is as a rule started by means of one of the conventional initiators of free-radical polymerization. These include thermal initiators such as azo compounds, for example azoisobutyronitrile (AIBN), or peroxides, for example benzoyl peroxides, or redox initiator systems such as a mixture of iron(III) acetylacetonate, benzoin and benzoyl peroxide, or photochemical free-radical formers such as benzoin or benzil methylketal.

The copolymerization can be carried out in solution. The reaction temperature is in general within the range from 10° to 200° C., preferably between 40° and 150° C. and particularly preferably between 40° and 100° C.

Solvents which may be present must be inert under the reaction conditions. Suitable solvents are, inter alia, aromatic hydrocarbons, chlorinated hydrocarbons, ketones and ethers. Examples thereof are benzene, toluene, xylene, ethylbenzene, isopropylbenzene, ethylene chloride, propylene chloride, methylene chloride, chloroform, methyl ethyl ketone, acetone, cyclohexanone, diethyl ether or tetrahydrofuran.

Another way of preparing the polymeric β-keto-ester acetals according to the invention is the acetalization of polymeric β-keto-esters, which are obtained by free-radical polymerization of compounds of the formula III, if appropriate together with the comonomers of the formula XVIa. The compounds of the formula IV or of the formulae V and VI can then be employed for the acetalization.

As mentioned at the outset, the polymeric β-keto-ester acetals according to the invention are valuable solution inhibitors for positive photoresists, which have a very good high sensitivity to acids and, together with acid-generating photoinitiators, form a radiation-sensitive mixture. The sensitivity of the polymeric β-keto-ester acetals according to the invention to acids persists even in high layer thicknesses, for example in 30 μm. In addition, the polymeric β-keto-esters obtained by acid cleavage from the polymeric compounds according to the invention are soluble in bases. By contrast, the polymeric β-keto acetals according to the invention are very stable to bases, so that very good differentiation between exposed and unexposed areas is obtained in the photoresist.

The invention thus also comprises a radiation-sensitive mixture which contains, relative to the total quantity of components a) and b), 85 to 99% by weight of a) a polymeric β-keto-ester acetal having the structural units of the formula XIV or XV and, if appropriate, of the formula XVI, and b) 1 to 15% by weight of a substance which forms an acid under the action of actinic radiation.

Preferably, the radiation-sensitive mixture contains 90 to 99% by weight, in particular 95 to 98% by weight, of component a) and 1 to 10% by weight, in particular 2 to 5% by weight, of component b).

A large number of compounds are known as radiation-sensitive components b) which, under the action of light, form or eliminate an acid. These include, for example, diazonium salts such as are used in the diazo process, o-quinone-diazides such as are used in known positive-working copying compositions, or also halogen compounds which form a hydrohalic acid under irradiation. Compounds of this type are described, for example, in U.S. Pat. Nos. 3,515,552, 3,536,489 or 3,779,778, and in German Offenlegungsschriften 2,718,259, 2,243,621 or 2,610,842.

However, cationic photoinitiators from the group of iodonium or sulfonium salts are also suitable as radiation-sensitive components b) of the compositions according to the invention. Such compounds are described, for example, in "UV-Curing, Science and Technology" (Editor: S. P. Pappas, Technology Marketing Corp., 642 Westover Road, Stanford, Conn., USA). In particular, diaryliodosyl salts can also be used. Such compounds are described, for example, in EP-A 106,797.

The sulfoxonium salts can also be used as radiation-sensitive compounds. Such salts are described, for example, in European Patent 35,969 or in EP-A 44,274 or 54,509. Aliphatic sulfoxonium salts which absorb in the far UV region should be mentioned in particular.

In particular, those compounds can also be used which release sulfonic acids when irradiated with actinic light. Such compounds are known per se and are described, for example, in GB-A 2,120,263, EP-A 84,515, 37,512 or 58,638 or in U.S. Pat. Nos. 4,258,121 or 4,371,605.

When salts are used as the radiation-sensitive acid-releasing components b), these are preferably soluble in organic solvents. With particular preference, these salts are precipitation products with complex acids, for example of fluoboric acid, hexafluorophosphonic acid, hexafluoroarsenic acid or hexafluoroantimonic acid.

If appropriate, binders (c) can also be added to the radiation-sensitive mixtures according to the invention, and this is particularly advantageous if the light-sensitive compositions are liquid or low-viscosity mixtures or if the mixtures contain a homopolymeric $\beta$-keto-ester acetal. In this case, the $\beta$-keto-ester acetal acts as the conventional solution inhibitor. After exposure, the polymeric $\beta$-keto-ester acetal re-forms, by acid-catalysed hydrolysis, the polymeric $\beta$-keto-ester which is soluble in bases and no longer inhibits dissolution of the base-soluble binder polymer.

It is also possible, however, to use a copolymer, which was prepared with the use of base-soluble comonomers as the compound of the formula XVIa, as the polymeric $\beta$-keto-ester acetal. Such copolymers combine the properties of a solution inhibitor with those of a binder, so that it is not absolutely necessary in this case to add an additional binder (c) to the radiation-sensitive mixture.

The quantity of the binder (c) can amount to 30-90% by weight, preferably 60-90% by weight, relative to the total quantity of components a), b) and c).

The binder is selected depending on the fields of application and the properties required therefor, such as ability to be developed in aqueous and aqueous-alkaline solvent systems or adhesion to substrates.

Examples of suitable binders c) are novolaks which are derived from an aldehyde, preferably formaldehyde, acetaldehyde or furfuraldehyde, but in particular from formaldehyde, and a phenol. The phenolic component of these binders is preferably phenol itself, or also a halogenated phenol, for example a phenol which is monosubstituted to disubstituted by chlorine atoms, preferably p-chlorophenol, or it is a phenol which is monosubstituted to disubstituted by $C_1$-$C_9$alkyl groups, for example o-, m- or p-cresol, a xylenol, p-tert-butylphenol or p-nonylphenol. The phenol component of the preferred novolaks can, however, also be p-phenylphenol, resorcinol, bis-(4-hydroxyphenyl)-methane or 2,2-bis-(4-hydroxyphenyl)-propane.

A part of the phenolic hydroxy groups of these novolaks can, if appropriate, have been modified by reaction with chloroacetic acid, isocyanates, epoxides or carboxylic acid anhydrides.

Examples of further suitable binders are copolymers of maleic anhydride with styrene or vinyl ethers or 1-alkenes. Further binders which can be used are: homopolymeric and copolymeric acrylates and methacrylates, for example copolymers of methyl methacrylate/ethyl acrylate/methacrylic acid, poly(alkyl methacrylates) or poly(alkyl acrylates), where alkyl=$C_1$-$C_{20}$.

Preferably, the binder used is an alkali-soluble substance, for example a novolak (if appropriate modified as described above), a copolymer of maleic anhydride with styrene or vinyl ethers or 1-alkenes, as well as a copolymer of esters of acrylic acid or methacrylic acid with ethylenically unsaturated acids, for example methacrylic acid or acrylic acid.

If appropriate, yet further additive resins can also be added to these alkali-soluble binders, as is customary in the case of the positive systems based on diazoketones. These additive resins include, for example, vinyl polymers such as polyvinyl acetate, polyacrylates, polyvinyl ethers or polyvinylpyrrolidones. In general, however, not more than 20% by weight, relative to the quantity of alkali-soluble binder, of these additive resins are added.

The compositions according to the invention can contain further conventional additives, for example stabilizers, pigments, dyes, fillers, adhesion promoters, flow agents, wetting agents and plasticizers. For application, the compositions can also be dissolved in suitable solvents.

The compositions according to the invention are outstandingly suitable as coating agents for substrates of any type, for example wood, textiles, paper, ceramics, glass, plastics such as polyesters, polyethylene terephthalate, polyolefins or cellulose acetate, in particular in the form of films, and also metals such as Al, Cu, Ni, Fe, Zn, Mg or Co, and GaAs, Si or $SiO_2$, on which an image is to be formed by imagewise exposure. A further subject of the present invention are the coated substrates.

In addition, the invention also relates to a process for producing positive images, which comprises the following working steps:

a) coating a substrate with a radiation-sensitive composition as defined above, b) exposure of the coated substrate with a predetermined pattern of actinic radiation and c) development of the coated substrate.

The coated substrates can be produced, for example, by preparing a solution or suspension of the composition.

The selection of the solvent and the concentration depend mainly on the type of composition and on the coating process. The solution is evenly applied to a substrate by means of known coating processes, for example by whirler-coating, dipping, blade coating, curtain coating processes, brushing, spraying and especially by electrostatic spraying and reverse roller coating. It is also possible to apply the light-sensitive layer to a temporary, flexible support and then to coat the final substrate, for example a copper-laminated circuit board, by layer transfer via lamination.

The quantity applied (layer thickness) and the nature of the substrate (layer carrier) depend on the desired field of application. It is a particular advantage that the compositions according to the invention can be employed in relatively widely variable layer thicknesses. This layer thickness range comprises values from about 0.5 $\mu$m up to more than 100 $\mu$m. With conventional positive systems based on naphthoquinonediazide, layer thicknesses of more than 10 $\mu$m can no longer be used.

Possible fields of application of the compositions according to the invention are the use as photoresists for electronics (electroplating resist, etch resist, folder resist), the production of printing plates such as offset printing plates or screen printing formes, the use in chemical milling or the use as a microresist in the production of integrated circuits.

The possible layer carriers and the processing conditions of the coated substrates vary correspondingly.

For example, films of polyester, cellulose acetate or plastic-coated papers are used for the photographic recording of information; specially treated aluminium is used for offset printing formes and copper-laminates are used for the production of printed circuits. The layer thicknesses for photographic materials and offset printing formes are about 0.5 $\mu$m to 10 $\mu$m, and 1 to about 100 $\mu$m for printed circuits.

After coating, the solvent is removed as a rule by drying, and a layer of the photoresist on the carrier results. After the imagewise exposure of the material, carried out in the usual way, the exposed areas of the photoresist are removed by dissolution in a developer.

The selection of the particular developer depends on the type of the photoresist, in particular on the nature of the binder used or of the photolysis products formed. The developer can comprise aqueous solutions of bases, to which organic solvents or mixtures thereof are added, if appropriate. The use of an aqueous solution of a base as the developer is preferred. Acids cannot be used, since their use would lead to cleavage of the $\beta$-acetal ester or $\beta$-ketal ester (or of the corresponding amide) in the unexposed areas of the coated substrate, and would thus entail detachment of the entire resist layer.

Particularly preferred developers are aqueous-alkaline solutions, such as are also used for developing naphthoquinone-diazide layers. These include, in particular, aqueous solutions of alkali metal silicates, phosphates, hydroxides and carbonates. If appropriate, minor amounts of wetting agents and/or organic solvents can also have been added to these solutions.

Examples of typical organic solvents which can be added to the developer fluids are cyclohexanone, 2-ethoxyethanol, toluene, acetone and mixtures of two or more of these solvents.

The term 'exposure with a predetermined pattern of actinic radiation' comprises both exposure through a photomask containing a predetermined pattern, for example a positive transparency, and exposure by a laser beam which is moved, for example by computer control, across the surface of the coated substrate, and in this way produces an image.

The light-sensitivity of the compositions according to the invention extends as a rule from the UV region (about 200 nm) up to about 600 nm and thus spans a very wide range. A large number of the most diverse types of light sources are therefore used. Both point sources of light and extended light sources (lamp carpets) are suitable. Examples are: carbon arc lamps, xenon arc lamps, mercury vapour lamps, if appropriate doped with metal halides (metal halogen lamps), fluorescent lamps, incandescent argon lamps, electronic flash lamps, photographic floodlights and X-rays. The distance between the lamp and the image material according to the invention can vary depending on the application and the type or intensity of the lamp, for example between 2 cm and 150 cm. Laser light sources, for example argon ion lasers or krypton ion lasers with strong emission lines (Ar lasers) at 457, 476, 488, 514 and 528 nm, are especially suitable. With this type of exposure, a photomask in contact with the photopolymer layer is no longer necessary; the controlled laser beam writes directly on the layer. The high sensitivity of the materials according to the invention is here very advantageous, allowing high writing speeds at relatively low intensities. Printed circuits in the electronics industry, lithographic offset printing plates or relief printing plates as well as photographic image-recording materials can be produced by this method.

If appropriate, the light-sensitive compositions can also contain sensitizers in order to enhance the spectral sensitivity in a particular region of the electromagnetic spectrum. These sensitizers include, for example, Michler's ketone, benzophenones, thioxanthones or aromatic hydrocarbons such as anthracene, pyrene or perylene. 9-Methylanthracene and 9,10-diethoxyanthracene are especially suitable.

Irradiation by electron beams is a further possible imaging method. Electron beams can thoroughly decompose the composition according to the invention and, in some cases, also crosslink it, so that a negative image is formed when the unirradiated parts are removed by a solvent or by exposure without an original and developing. By contrast, at low intensity and/or higher writing speed of the electron beam, the electron beam effects a differentiation in the direction of higher solubility, i.e. the irradiated layer parts can be removed by the developer. If the process is carried out with electron beams, acid donors which have absorption regions in the shorter-wavelengths part of the electromagnetic spectrum and are therefore less sensitive to daylight are also suitable, in addition to the known photolytic acid donors sensitive to visible and near UV light. This has the advantage that the recording materials can be handled without excluding light and that the materials can be provided with better storage stability. Examples of such starters are tribromomethylphenylsulfone, 2,2',4,4',6,6'-hexabromodiphenylamine, pentabromomethane, 2,3,4,5-tetrachloroaniline, pentaerythritol tetrabromide, Clophen resin W, i.e. a chloroterphenyl resin, or chlorinated paraffins.

The compositions according to the invention can be used in the most diverse fields of application. They are used in particular where a photolithographic image with high resolution is to be produced.

The invention therefore also relates to the use of the compositions, as defined above, as positive photoresists for the production of printing formes, printed circuit boards or integrated circuits, and for silver-free photographic films. The invention also relates to the printing formes, printed circuit boards or integrated circuits or silver-free photographic films produced with the use of said compositions.

EXAMPLE 1

Preparation of α-(2-methyl-1,3-dioxolan-2-yl)-acetoxyethyl methacrylate [(2-methyl-1,3-dioxolan-2-yl)-8-oxo-7-oxa-4-oxa-3-oxo-2-methyl-1-nonene]

21.4 g (0.1 mol) of 2-acetoacetoxyethyl methacrylate, 18.62 g (0.3 mol) of ethylene glycol and 0.19 g (1 mmol) of p-toluenesulfonic acid monohydrate (1 mol % of p-TsOH) are dissolved in 200 ml of benzene and boiled under reflux under a water separator. 1.7 g (5 mol %) of 2,2,4,6-Ralox ® [2.2'-methylene-bis-(4,6-di-tert-butyl-phenol), a commercial product from Raschig GmbH, Germany] are added as a polymerization inhibitor.

After 3 hours, 1.9 ml of water (theoretical amount: 1.8 ml) have been separated off. The benzene is distilled off, and the residue is dissolved in 150 ml of ether and extracted twice with 75 ml of saturated sodium carbonate solution and once with 75 ml of saturated sodium chloride solution. The combined aqueous phases are extracted once more with 50 ml of ether. The combined organic phases are dried over MgSO4, filtered and concentrated in a rotary evaporator. This gives 26.2 g of a colourless residue [87% pure according to gas chromatography (GC)]. The residue is subjected to fractional distillation in a high vacuum at 0.02 mbar. This gives 21.1 g of a colourless oil (boiling point: 107°–115° C./0.02 mbar; GC>95%), which corresponds to a yield of 81% of theory. The weight of the distillation residue is 3.8 g.

Elemental analysis: Calculated: C=55.81%; H=7.03%; Found: C=55.73%; H=7.07%.

The data of the IR, $^1$H-NMR and $^{13}$C-NMR spectra confirm that this is a compound of the formula

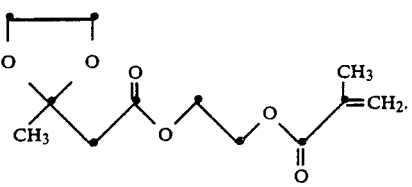

EXAMPLE 2

Preparation of α-(2-methyl-1,3-dioxan-2-yl)-acetoxyethyl methacrylate

As described in Example 1, the above compound is prepared from 2-acetoacetoxyethyl methacrylate (107.1 g) and 1,3-propanediol (41.9 g) in benzene (1000 ml) with p-TsOH catalysis under a water separator. Yield: 52% of theory; GC~90% pure after distillation in a thin-layer evaporator.

The data of the IR and $^1$H-NMR spectra confirm that a compound of the formula

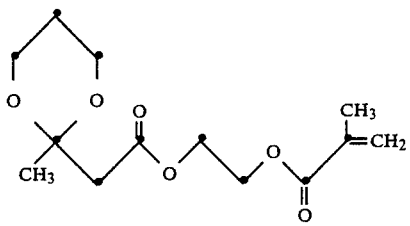

is obtained.

EXAMPLE 3

Preparation of α-(5-butyl-2-methyl-1,3-dioxolan-2-yl)-acetoxyethyl methacrylate

As described in Example 1, the above compound is prepared from 2-acetoacetoxyethyl methacrylate (42.8 g) and 1,2-hexanediol (26 g) in benzene (200 ml) with p-TsOH catalysis under a water separator. Yield: 77% of theory, boiling point=130°–136° C./0.02 mbar.

Elemental analysis: Calculated: C=61.13%; Found: C=61.4%; Calculated: H=8.34%; Found: H=8.36%.

The data of the IR and $^1$H-NMR spectra confirm that a compound of the formula

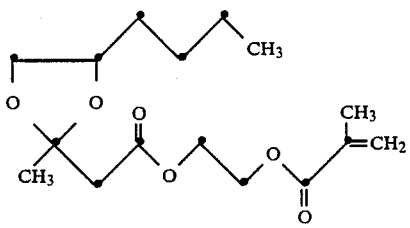

is obtained.

EXAMPLE 4

Preparation of α-(2,4,5-trimethyl-1,3-dioxolan-2-yl)-acetoxyethyl methacrylate

As described in Example 1, the above compound is prepared from 2-acetoacetoxyethyl methacrylate (42.8 g) and 2,3-butanediol (19 g) in benzene (200 ml) with p-TsOH catalysis under a water separator, yield: 63% of theory; boiling point 107°–109° C./0.02 mbar. GC=95% pure.

Elemental analysis: Calculated: C=58.73%; Found: C=58.68%; Calculated: H=7.75%; Found: H=7.71%.

The data of the IR and $^1$H-NMR spectra confirm that a compound of the formula

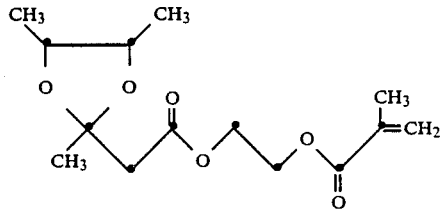

is obtained.

EXAMPLE 5

Preparation of α-(2-phenyl-1,3-dioxolan-2-yl)-acetoxyethyl methacrylate a) 192.2 g (1 mol) of ethyl benzoylacetate and 186.2 g (3 mol) of ethylene glycol are heated within one hour to 260° C. in a distillation apparatus. After one further hour, 5 ml of ethanol has distilled off. The distillation head is replaced by a water separator, and 3.44 g (20 mmol) of p-TsOH and 1 l of benzene are added. After boiling for 10 hours under reflux, 18 ml of water have separated off. The product is isolated as described in Example 1.

After double distillation in a thin-layer evaporator, 28 g of a colourless oil are obtained. Yield: 11% of theory; GC>95% pure.

Elemental analysis: Calculated: C=61.9%; Found: C=61.69%; Calculated: H=6.39%; Found: H=6.43%.

The data of the IR and $^1$H-NMR spectra confirm that a compound of the following formula

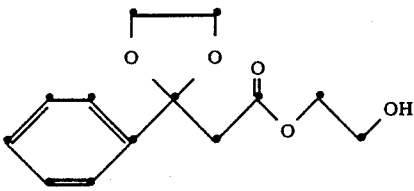

is obtained.

b) 63 g (0.25 mol) of the compound prepared under a), 28.8 g (0.275 mol) of methacryloyl chloride and 0.85 g of 2,2,4,6-Ralox ® are dissolved in 400 ml of ether, and a solution of 23.7 g (0.3 mol) of pyridine in 100 ml of ether is added dropwise at room temperature in the course of 1 hour. After stirring at room temperature for 72 hours, the white suspension is poured into ice water. The organic phase is washed twice with 150 ml of 1N NaHCO$_3$ solution, dried over MgSO$_4$, filtered and concentrated. Distillation in a high vacuum gives 31 g of a colourless oil. Yield: 39% of theory, boiling point: 142°–144° C./0.02 mbar; GC~92% pure.

Elemental analysis: Calculated: C=63.74%; Found: C=63.67%; Calculated: H=6.29%; Found: H=6.36%.

EXAMPLE 6

Preparation of α-(2-methyl-1,3-dioxolan-2-yl)-acetoxyethyl methacrylate a) 200.3 g (2 mol) of ethyl acetoacetate and 248.5 g (4 mol) of ethylene glycol are heated to 140° C. under normal pressure in a distillation apparatus; after 3 hours, 115 ml of ethanol have distilled off (theoretical quantity: 114 ml). The reaction is allowed to continue for a further 2 hours at 180° C., and a further 10 ml of ethanol distil over. Fractional distillation is then carried out in a vacuum of 0.01 mbar. This gives 129.8 g of a colourless oil (boiling point: 75°–85° C./0.01 mbar), which corresponds to a yield of 44% of theory.

Elemental analysis: Calculated: C=49.31%; H=6.90%; Found: C=49.16%; H=6.87%.

The data of the IR and $^1$H-NMR spectra confirm that the compound obtained is 2-hydroxyethyl 3-oxobutyrate.

b) 14.6 g (0.1 mol) of the compound prepared under a) and 6.83 g (0.1 mol) of ethylene glycol are acetalized with 5 mmol of p-TsOH as catalyst, as in Example 1. Yield 62% (of theory); boiling point: 85°–91° C./0.03 mbar; GC~93% pure.

Elemental analysis: Calculated: C=50.52%; H=7.42%; Found: C=50.65%; H=7.41%.

The data of the IR and $^1$H-NMR spectra confirm that a compound of the formula

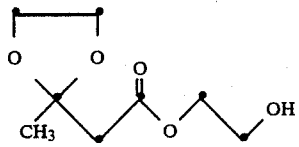

is obtained.

c) 9.5 g (0.05 mol) of the compound prepared under b) and 5.6 g (0.055 mol) of triethylamine are dissolved in 200 ml of diethyl ether. At room temperature (RT), 5.75 g (0.055 mol) of methacryloyl chloride, dissolved in 100 ml of diethyl ether, are added dropwise in the course of 20 minutes and the reaction solution is stirred for 1 further hour at the reflux temperature of the ether. The mixture is filtered over basic Alox (alumina) and the filtrate is concentrated, 4.3 g of an oil being obtained which, according to GC, consists to the extent of 76% of pure α-(2-methyl-1,3-dioxolan-2-yl)-acetoxyethyl methacrylate.

EXAMPLE 7

Preparation of α-(2,2-dimethoxyethyl)-acetoxyethyl methacrylate

Acetoacetoxyethyl methacrylate is dissolved in methanol and, as described by F. Gasparrini et al in Tetrahedron 1984, 40, 1491-1500, modified silica gel is added and the mixture is stirred at room temperature. The catalyst is filtered off and the residue is concentrated. The product is purified by chromatography. The yield of pure product is 65% of theory; GC=92% pure. The corresponding enol ether is isolated as a by-product.

Elemental analysis: Calculated: C=55.37%; H=7.75%; Found: C=55.58%; H=7.75%.

The data of the IR and $^1$H-NMR spectra confirm that a compound of the formula

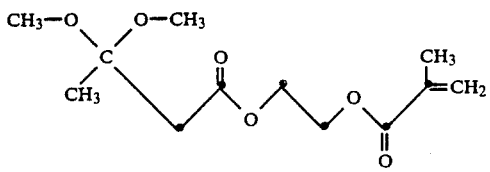

is obtained.

Preparation of Polymers or Copolymers from the Monomers of the Formulae I and II According to the Invention 0.5% by weight of α,α'-azoisobutyronitrile is added to a 20% solution of the monomer in tetrahydrofuran in a polymerization tube. The solution is evacuated at 0° C. to 30 mbar in the course of 30 seconds and flooded with argon. The procedure is repeated three times. Subsequently, the polymerization tube is sealed, and polymerization is carried out at 65° C. for 24 hours. The polymer is isolated by precipitation and, if necessary, purified by reprecipitation. After drying, the polymer is characterized by gel permeation chromatography (GPC) with polystyrene as standard, by the IR and $^1$H-NMR spectra and by elemental analysis. The results are compiled in Table 1.

TABLE 1

| Example | Monomer according to Example | Co-monomer | Mw | Mn | $n\frac{Mw}{Mn}$ | Calculated C | H | Found C | H |
|---|---|---|---|---|---|---|---|---|---|
| A | 100% 1 | — | 81600 | 24500 | 3.3 | 55.81 | 7.02 | 55.66 | 7.09 |
| B | 88% 1 | 12% MAS[x] | 89100 | 30300 | 2.9 | 55.81 | 7.03 | 55.64 | 7.06 |
| C | 90% 1 | 10% MAS | 142700 | 24200 | 5.9 | 55.81 | 7.03 | 55.70 | 7.19 |
| D | 100% 2 | — | 84800 | 26800 | 3.2 | 57.34 | 7.40 | 57.17 | 7.38 |
| E | 40% 2 | 60% AA[xx] | 113000 | 25600 | 4.4 | 56.65 | 6.96 | 56.22 | 7.03 |
| F | 25% 2 | 75% AA | 72800 | 21000 | 3.5 | 56.44 | 6.83 | 56.19 | 6.77 |
| G | 10% 2 | 90% AA | 81000 | 18900 | 4.3 | 56.23 | 6.69 | 55.93 | 6.87 |
| H | 100% 3 | — | 85000 | 14000 | 6 | 61.13 | 8.34 | 60.96 | 8.26 |
| I | 100% 4 | — | 79300 | 13400 | 5.9 | 58.73 | 7.75 | 58.58 | 7.66 |
| J | 100% 5 | — | 72100 | 15600 | 4.6 | 63.74 | 6.29 | 63.57 | 6.41 |

[x]MAS = methacrylic acid
[xx]AA = acetoacetoxymethyl methacrylate

APPLICATION EXAMPLES

EXAMPLE I

For the preparation of coating solutions, the components indicated in Table 2 are dissolved in 1-acetoxy-2-ethoxyethane in such a way that a 30% by weight solution is obtained. In addition to the light-crosslinkable polymer and a binder, the coating solution contains, relative to the quantity of polymer and binder, 5% by weight of photoinitiator, 1% by weight of sensitizer ($A_1$ = 9-methylanthracene, B = 9,10-diethoxyanthracene), 0.5% by weight of the wetting agent Fluorad ® FC 430 (3M) and 0.2% by weight of the dye Orasol Red ® B (Ciba-Geigy AG).

A cleaned copper-laminated circuit board is coated by means of wire draw bar with the coating solution; wet film thickness 100 μm. The boards are dried for 30 minutes at 80° C., the resulting layer thickness being 25–30 μm, measured by an isoscope MP (Helmut Fischer Elektronik and Messtechnik AG). The coated boards are exposed through a Stouffer resolution and sensitivity guide (optical density increments 0.15). The light source used is a 5000 W metal halogen lamp (Sylvania M061). The distance from the vacuum frame is 65 cm. The exposure time is quoted in pulses of the Staub exposure meter. The exposed boards are developed with the appropriate developer by gentle rubbing with a cottonwool swab.

Developer $A_2$:
75 g of sodium metasilicate.5H$_2$O
0.4 g of Supronic ® B50 (ABM Chemicals Ltd., Stockport, Cheshire SK6 1PQ/GB)
925 g of deionized water.
$B_1$: Developer A and water (1:1).

TABLE 2

| Polymer/ % by weight | Binder/ % by weight | Photo-initiator | Sensitizer | Exposure time (pulses) | Developer/ developing time (seconds) | Wedge steps attacked | developed | Image quality |
|---|---|---|---|---|---|---|---|---|
| A/30 | Novolak[1]/70 | a | $A_1$ | 120 | $A_2$/420 | 4 | 3 | ++ |
|  |  |  |  | 240 | $A_2$/420 | 10 | 9 | ++ |
| A/25 | Novolak/75 | a | $A_1$ | 60 | $A_2$/120 | 4 | 3 | ++ |
|  |  |  |  | 120 | $A_2$/120 | 7 | 6 | ++ |
|  |  |  |  | 240 | $A_2$/120 | 9 | 8 | ++ |
| A/20 | Novolak/80 | a | $A_1$ | 60 | $A_2$/90 | 6 | 4 | ++ |
|  |  |  |  | 120 | $A_2$/90 | 11 | 9 | + |
|  |  |  |  | 240 | $A_2$/90 | 12 | 10 | +/− |

[1]Alnovol PN 430 (from Hoechst)
[a]2-(Methoxystyryl)-4,6-bis(trichloromethyl)-s-triazine
++ = very good
+ = good
− = poor

EXAMPLE II

Mixtures of polymer A and novolak in a mixing ratio of 25 to 75% by weight in each case are provided with various photo-initiators, the following being used.

Photoinitiator:
a) 2-(4-Methoxystyryl)-4,6-bis(trichloromethyl)-s-triazine

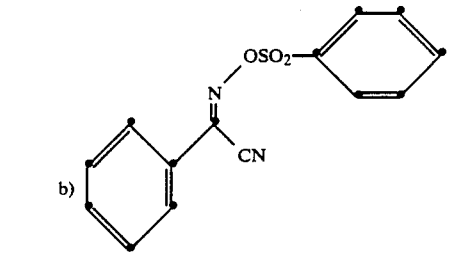

c) Ph$_3$S$^+$PF$_6^\ominus$ (triphenylsulfonium hexafluorophosphate)

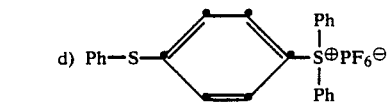

("UVI ® 6974" from General Electric)

e) Ph₃S+SbF₆⁻ (triphenylsulfonium hexafluoroantimonate)
f) Ph₂J+PF₆⊖ (diphenyliodonium hexafluorophosphate)

The properties of the images produced from the light-sensitive mixtures are shown in Table 3. The values given in brackets are obtained by heat-treating the board, after exposure, for 30 minutes at 40° C.

TABLE 3

| Polymer/ % by weight | Binder/ % by weight | Photo-initiator | Sensitizer | Exposure time (pulses) | Developer/ developing time (seconds) | Wedge steps attacked | Wedge steps developed | Image quality |
|---|---|---|---|---|---|---|---|---|
| A/25 | Novolak/75 | a | A₁ | 60 | A₂/90 | 4 | 3 | ++ |
|  |  |  |  | 120 | A₂/90 | 7 | 6 | ++ |
| A/25 | Novolak/75 | b | A₁ | 120 | A₂/90 | 6(7) | 3(5) | ++ |
| A/25 | Novolak 75 | c | A₁ | 60 | A₂/90 | 5 | 4 | ++ |
|  |  |  |  | 120 | A₂/90 | 9 | 7 | ++ |
| A/25 | Novolak/75 | d | A₁ | 30 | A₂/90 | −(1) | −(2) | /++ |
|  |  |  |  | 60 | A₂/90 | −(7) | −(5) | /++ |
|  |  |  |  | 120 | A₂/90 | 3 | 5 | ++/ |
| A/25 | Novolak/75 | e | A₁ | 30 | A₂/90 | −(10) | −(4) | /+ |
|  |  |  |  | 60 | A₂/90 | 11(11) | 4(5) | +/+ |
| A/25 | Novolak/75 | f | A₁ | 30 | A₂/90 | 5 | 3 | ++/ |
|  |  |  |  | 60 | A₂/90 | 6(11) | 5(9) | ++/+ |
|  |  |  |  | 120 | A₂/90 | 13(11) | 11 | +/− |
| A/25 | Novolak/75 | g | A₁ | 10 | A₂/90 | −(5) | −(2) | /++ |
|  |  |  |  | 30 |  | 5(6) | 3(4) | ++/++ |
|  |  |  |  | 60 |  | 8(9) | 5(7) | ++/++ |
| A/25 | Novolak/75 | h | A₁ | 10 | A₂/90 | −(6) | −(4) | /+ |
|  |  |  |  | 30 | A₂/90 | 10(10) | 7(8) | +/+ |
| A/25 | Novolak/75 | i | A₁ | 15 | A₂/90 | 6(5) | 1(1) | ++/++ |
|  |  |  |  | 30 | A₂/90 | 8(8) | 4(5) | ++/++ |
|  |  |  |  | 60 | A₂/90 | 10(15) | 5(10) | ++/+ |
| A/25 | Novolak/75 | k | B | 5 | A₂/90 | 8(9) | 2(3) | +/+ |
|  |  |  |  | 10 | A₂/90 | 8(6) | 3(3) | +/++ |
|  |  |  |  | 30 | A₂/90 | 8(10) | 5(7) | ++/++ | g) Ph₂J+AsF₆⁻ (diphenyliodonium hexafluoroarsenate)
h) Ph₂J+SbF₆⁻ (diphenyliodonium hexafluoroantimonate)

i) 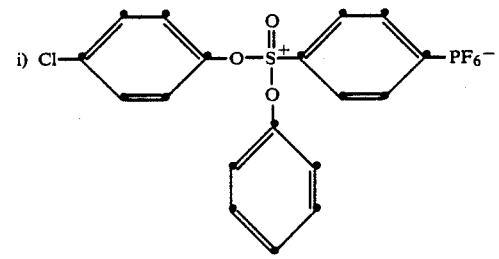

EXAMPLE III

Using polymer D and certain photoinitiators, light-sensitive mixtures are prepared and copper-laminated boards are coated with them, as in Example 1. After 90 seconds' exposure, the boards are heat- treated for 30 minutes at 40° C. The properties of the images obtained are shown in Table 4.

TABLE 4

| Polymer/ % by weight | Binder/ % by weight | Photo-initiator | Sensitizer | Exposure time (pulses) | Developer | Wedge steps attacked | Wedge steps developed | Image quality |
|---|---|---|---|---|---|---|---|---|
| D/25 | Novolak/75 | a | B | 1 | B₁ | 2 | 0 | − |
|  |  |  |  | 5 | B₁ | 5 | 2 | ++ |
|  |  |  |  | 10 | B₁ | 9 | 5 | ++ |
|  |  |  |  | 30 |  | 14 | 10 | ++ |
| D/25 | Novolak/75 | b | B | 10 | B₁ | 10 | 4 | + |
|  |  |  |  | 30 | B₁ | 11 | 6 | + |
| D/25 | Novolak/75 | c | B | 5 | B₁ | 0 | 0 |  |
|  |  |  |  | 10 | B₁ | 4 | 1 | + |
|  |  |  |  | 30 | B₁ | 10 | 7 | + |
| D/25 | Novolak/75 | f | A₁ | 1 | B₁ | 0 | 0 | − |
|  |  |  |  | 10 | B₁ | 9 | 6 | ++ |
|  |  |  |  | 30 | B₁ | 12 | 9 | ++ |
| D/25 | Novolak/75 | f | B | 1 | B₁ | 4 | 1 | + |
|  |  |  |  | 10 | B₁ | 8 | 4 | ++ |
|  |  |  |  | 30 | B₁ | 11 | 8 | ++ |
| D/25 | Novolak/75 | g | B | 1 | B₁ | 5 | 1 | ++ |
|  |  |  |  | 10 | B₁ | 10 | 6 | ++ |
|  |  |  |  | 30 | B₁ | 11 | 8 | ++ |
| D/25 | Novolak/75 | h | B | 1 | B₁ | 6 | 2 | ++ |
|  |  |  |  | 10 | B₁ | 9 | 7 | ++ |
|  |  |  |  | 30 | B₁ | 12 | 10 | ++ |
| D/25 | Novolak/75 | i | B | 2 | B₁ | 6 | 2 | ++ |
|  |  |  |  | 10 | B₁ | 15 | 7 | ++ |
|  |  |  |  | 30 | B₁ | 14 | 10 | ++ |

EXAMPLE IV

Using various polymers, light-sensitive coating solutions are prepared as in Example I, which each contain 5% by weight of photoinitiator f and 1% by weight of sensitizer $A_1$. After copper-laminated boards have been coated with these coating solutions, the boards are exposed and developed as in Example 1. The properties of the images obtained are shown in Table 5.

TABLE 5

| Polymer/ % by weight | Binder/ % by weight | Exposure time (pulses) | Developer | Wedge steps attacked | Wedge steps developed | Image quality |
|---|---|---|---|---|---|---|
| A/25 | Novolak/75 | 30 | $A_1$ | 5 | 3 | ++ |
|  |  | 60 | $A_1$ | 6 | 5 | ++ |
|  |  | 120 | $A_1$ | 13 | 11 | ++ |
| B/25 | Novolak/75 | 30 | $B_1$ | 5 | 3 | ++ |
|  |  | 60 | $B_1$ | 8 | 6 | ++ |
|  |  | 120 | $B_1$ | 12 | 10 | ++ |
| C/25 | Novolak/75 | 30 | $B_1$ | 3 | 1 | ++ |
|  |  | 60 | $B_1$ | 6 | 4 | ++ |
|  |  | 120 | $B_1$ | 11 | 9 | ++ |
| D/25 | Novolak/75 | 10 | $B_1$ | 9 | 6 | ++ |
|  |  | 30 | $B_1$ | 12 | 9 | ++ |
|  |  | 60 | $B_1$ | >15 | >15 | + |
| I/25 | Novolak/75 | 30 | $B_1$ | 2 | 0 | − |
|  |  | 60 | $B_1$ | 4 | 1 | ++ |
|  |  | 120 | $B_1$ | 8 | 5 | ++ |
| J/25 | Novolak/75 | 30 | $A_1$ | 6 | 4 | ++ |
|  |  | 60 |  | 9 | 6 | ++ |

EXAMPLE V

Light-sensitive coating solutions, which all contain diphenyliodonium hexafluorophosphate as the photoinitiator, are prepared as in Example 1 from a polymer A with various alkali-soluble binders, i.e. a polymer with either phenolic hydroxyl groups or β-keto-ester side groups. The coating solutions are processed as in Example 1 to give images, the properties of which are shown in Table 6. The following binders are used:

Binder II: "Resin M" having an $M_w$ of about 6000, commercially available from Maruzen Oil Co.

Binder III: Copolymer of 4-hydroxyphenylmaleimide and butyl vinyl ether in a 1:1 molar ratio, prepared according to the instructions of S. R. Turner et al. in Polymer Eng. Science 26 (1986), pages 1096 to 1100.

Binder IV: Poly-(2-acetoacetoxyethyl methacrylate).

A mixture of 95 parts of a solution of 112 g of sodium metasilicate.$5H_2O$, 3 g of strontium hydroxide.$8H_2O$, 30 g of polyethylene glycol (15,000) and 5 g of levulinic acid in 10 liters of water and 5 parts of 1N NaOH is used as developer $C_1$.

TABLE 6

| Polymer/ % by weight | Binder/ % by weight | Exposure time (pulses) | Developer | Wedge steps attacked | Wedge steps developed | Image quality |
|---|---|---|---|---|---|---|
| A/50 | II/50 | 10 | $B_1$ | 2 | 0 | − |
|  |  | 30 | $B_1$ | 4 | 3 | ++ |
|  |  | 60 | $B_1$ | 7 | 5 | ++ |
|  |  | 120 | $B_1$ | 9 | 7 | ++ |
| A/40 | II/60 | 10 | $B_1$ | 4 | 1 | + |
|  |  | 30 | $B_1$ | 6 | 4 | ++ |
|  |  | 60 | $B_1$ | 9 | 6 | ++ |
|  |  | 120 | $B_1$ | 12 | 8 | ++ |
| A/30 | II/70 | 10 | $B_1$ | 14 | 4 | + |
|  |  | 30 | $B_1$ | 10 | 7 | ++ |
|  |  | 60 | $B_1$ | 14 | 10 | ++ |
|  |  | 120 | $B_1$ | 13 | 8 | ++ |
| A/25 | II/75 | 10 | $B_1$ | 6 | 1 | ++ |
|  |  | 30 | $B_1$ | 11 | 6 | ++ |
|  |  | 60 | $B_1$ | 10 | 6 | ++ |
|  |  | 120 | $B_1$ | 14 | 10 | + |
| A/10 | II/90 | 10 | $B_1$ | 4 | 1 | + |
|  |  | 30 | $B_1$ | 6 | 4 | ++ |
|  |  | 60 | $B_1$ | 9 | 6 | ++ |
|  |  | 120 | $B_1$ | 12 | 8 | + |
| A/40 | III/60 | 10 | $C_1$ | 6 | 0 | − |
|  |  | 30 | $C_1$ | 9 | 1 | + |
|  |  | 30 | $B_1$ | 10 | 4 | ++ |
|  |  | 60 | $C_1$ | 11 | 5 | ++ |
|  |  | 120 | $C_1$ | 14 | 6 | ++ |
| A/30 | III/70 | 10 | $C_1$ | 4 | 0 | − |
|  |  | 30 | $C_1$ | 9 | 2 | ++ |
|  |  | 60 | $C_1$ | 13 | 4 | ++ |
|  |  | 120 | $C_1$ | 15 | 7 | ++ |
| A/25 | III/75 | 10 | $B_1$ | 7 | 0 | − |
|  |  | 30 | $B_1$ | 9 | 2 | ++ |
|  |  | 60 | $B_1$ | 10 | 4 | ++ |
|  |  | 120 | $B_1$ | 14 | 7 | ++ |
| A/20 | III/80 | 10 | $B_1$ | 7 | 2 | ++ |

TABLE 6-continued

| Polymer/ % by weight | Binder/ % by weight | Exposure time (pulses) | Developer | Wedge steps attacked | Wedge steps developed | Image quality |
|---|---|---|---|---|---|---|
| | | 30 | B₁ | 9 | 4 | ++ |
| | | 60 | B₁ | 12 | 6 | ++ |
| | | 120 | B₁ | 14 | 8 | ++ |
| A/50 | IV/50 | 60 | B₁ | 16 | 3 | — |
| | | 120 | B₁ | 5 | 3 | ++ |
| | | 120 | C₁ | 7 | 5 | ++ |
| | | 240 | C₁ | 16 | 10 | + |

EXAMPLE VI

A 30% solution with the following components is prepared in ethyl glycol acetate:

50 parts of binder I (novolak according to Example 1)
50 parts of polymer A (Table 1)
5 parts of photoinitiator f
1 part of sensitizer B
0.5 part of Fluorad ® FC 430 wetting agent
0.2 part of Orasol Blue ® (from Ciba-Geigy AG)

A copper-laminated circuit board (35 μm Cu) is coated, as described in Example 1, with the solution, and exposed for 60 pulses (about 12 seconds) under a circuit board pattern. Development is carried out in a Convac spray developer for 25 seconds, using developer B₁, and the bared copper is then etched away for 15 minutes at 40° C. in a 15% sodium persulfate solution. The surface of the resist on the surface of the circuit tracks shows no visible changes under a microscope. The circuit tracks are laid bare by renewed exposure and development.

Another board is, after development, electroplated for 90 minutes in a bright copper bath from Erné. 10 μm of Cu are deposited. After electroplating, the resist shows no visible changes under the microscope. After renewed exposure, the resist can be detached in developer B₁.

EXAMPLE VII

As described in Example VI, boards are coated with the following solution, etched and electroplated:

50 parts of binder III
50 parts of polymer A
5 parts of photoinitiator f
1 part of sensitizer B
0.5 part of Fluorad ® FC 430 wetting agent
0.2 part of Orasol Red ® B The developed board is etched for 20 minutes at 40° C. in a 15% sodium persulfate solution. Under the microscope, the surface of the resist shows no visible changes. After renewed exposure and development, it was possible to detach the resist by means of developer C₁.

Another board is electroplated at 40° C. for 105 minutes; 10 μm of copper are deposited. The resist shows no change of the surface. After renewed exposure and development, the resist can be detached by means of developer E.

EXAMPLE VIII

An Si wafer is roller-coated with a 10% solution in ethyl glycol acetate; the resulting layer thickness is 1.2 μm, measured by means of an "Alpha Stepper 100" from Tencor.

Formulation:
75 parts of binder I 25 parts of polymer A
5 parts of photoinitiator f
1 part of sensitizer B
0.5 part of "FC 430" wetting agent.

One wafer in each case is exposed for 50, 100, 200 or 400 seconds through a test mask in an Oriel 500 W mercury xenon lamp. The exposed wafers are left to stand for 15 minutes at 40° C. and 1 hour at 20° C. The wafers are developed by dipping them into developer B₁. All 4 wafers show cleanly developed structures with steep edges up to a size of 1.5 μm.

What is claimed is:

1. A compound of the formula I or II

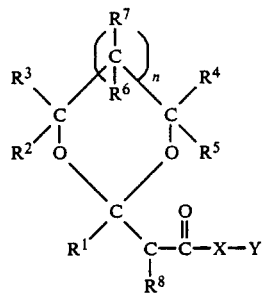

(I)

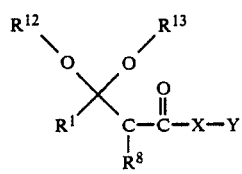

(II)

in which n is zero or the number 1, $R^1$ is hydrogen, $C_1$–$C_4$alkyl which is unsubstituted or substituted by a chlorine atom or atoms, a $C_2$–$C_4$alkyl interrupted by an ether oxygen atom or atoms, phenyl or benzyl, $R^2$, $R^3$, $R^4$, $R^5$, $R^6$ and $R^7$ independently of one another are each a hydrogen atom, chlorine atom, $C_1$–$C_6$alkyl or phenyl, $R^8$ is a hydrogen atom, phenyl, p-nitrophenyl, p-cyanophenyl or the radical —COOR⁹, in which $R^9$ is $C_1$–$C_6$alkyl or phenyl, X is an oxygen atom, Y is a radical of the formulae

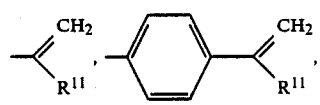

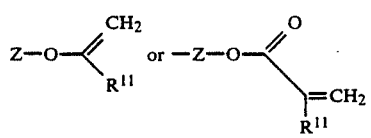

in which $R^{11}$ is a hydrogen atom or $C_1$-$C_4$alkyl, Z is one of the following radicals $-(CH_2)_b-$, $-CH_2-CH_2-(OCH_2-CH_2)_c OCH_2-CH_2-$, $-CH_2-CHR^{11}-$,

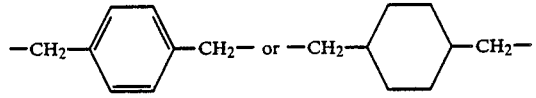

in which b is a number from 3 to 5 and c is zero or a number from 1 to 3, and $R^{12}$ and $R^{13}$ independently of one another are each $C_1$-$C_4$alkyl.

2. A compound of the formula I according to claim 1, in which n is zero or the number 1, $R^1$ is $C_1$-$C_4$alkyl, methoxymethyl or phenyl, $R^2$, $R^3$, $R^4$, $R^5$, $R^6$, $R^7$ and $R^8$ are each a hydrogen atom, X is an oxygen atom and Y is the radical

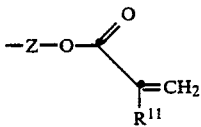

in which Z is ethylene and $R^{11}$ is a hydrogen atom or methyl.

3. A compound of the formula II according to claim 1, in which $R^1$, $R^{12}$ and $R^{13}$ independently of one another are each $C_1$-$C_4$alkyl, $R^8$ is a hydrogen atom, X is an oxygen atom and Y is a radical of the formula

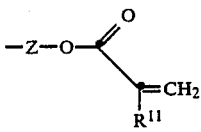

in which Z is ethylene and $R^{11}$ is a hydrogen atom or methyl.

* * * * *